US00RE49299E

(19) United States
(12) Reissued Patent
Karushev et al.

(10) Patent Number: US RE49,299 E
(45) Date of Reissued Patent: Nov. 15, 2022

(54) METHOD OF PRODUCING POROUS METAL-CARBON MATERIALS

(71) Applicant: POWERMERS INC., Westerville, OH (US)

(72) Inventors: Mikhail P. Karushev, St. Petersburg (RU); Svetlana A. Belous, St. Petersburg (RU); Tatyana S. Lavrova, St. Petersburg (RU); Irina A. Chepurnaya, St. Petersburg (RU); Alexander M. Timonov, St. Petersburg (RU); Semyon Kogan, Newton, MA (US)

(73) Assignee: Powermers Inc., Columbus, OH (US)

(21) Appl. No.: 15/896,622

(22) Filed: Feb. 14, 2018

Related U.S. Patent Documents

Reissue of:
(64) Patent No.: 9,653,736
Issued: May 16, 2017
Appl. No.: 14/825,402
Filed: Aug. 13, 2015

U.S. Applications:
(60) Provisional application No. 62/039,010, filed on Aug. 19, 2014.

(51) Int. Cl.

| | |
|---|---|
| ***B01J 20/00*** | (2006.01) |
| ***H01M 4/86*** | (2006.01) |
| ***C07F 15/04*** | (2006.01) |
| ***C07F 1/00*** | (2006.01) |
| ***B01J 20/20*** | (2006.01) |
| ***B01J 20/22*** | (2006.01) |
| ***B01J 20/32*** | (2006.01) |
| ***H01M 4/36*** | (2006.01) |
| ***H01M 4/90*** | (2006.01) |
| ***H01M 4/46*** | (2006.01) |
| ***C01B 32/05*** | (2017.01) |
| ***C25B 3/13*** | (2021.01) |
| *H01M 4/62* | (2006.01) |

(52) U.S. Cl.
CPC ..... *H01M 4/8652* (2013.01); *B01J 20/20* (2013.01); *B01J 20/226* (2013.01); *B01J 20/3204* (2013.01); *C01B 32/05* (2017.08); *C07F 1/005* (2013.01); *C07F 15/045* (2013.01); *C25B 3/13* (2021.01); *H01M 4/364* (2013.01); *H01M 4/366* (2013.01); *H01M 4/9075* (2013.01); *H01M 4/625* (2013.01); *H01M 4/8673* (2013.01)

(58) Field of Classification Search
CPC .... H01M 4/8652; H01M 4/364; H01M 4/366; H01M 4/9075; H01M 4/625; H01M 4/8673; B01J 20/20; B01J 20/226; B01J 20/3204; C01B 31/02; C07F 1/005; C07F 15/045; C25B 3/12
See application file for complete search history.

(56) References Cited

U.S. PATENT DOCUMENTS

| | | | | |
|---|---|---|---|---|
| 6,753,108 | B1 | 6/2004 | Hampden-Smith et al. | |
| 7,382,603 | B2 * | 6/2008 | Timonov | H01M 4/381 361/503 |
| 2007/0082805 | A1 | 4/2007 | Ohya et al. | |
| 2007/0234537 | A1 * | 10/2007 | Chepurnaya | H01G 9/038 29/25.03 |

FOREIGN PATENT DOCUMENTS

| | | | |
|---|---|---|---|
| WO | 2004/032162 | A1 | 4/2004 |
| WO | 2005/036572 | A1 | 4/2005 |

OTHER PUBLICATIONS

Karushev et al., "Adsorption-Electrochemical Modification of Nanoporous Carbon Materials by Nickel Complexes with Schiff Bases," Russian Journal of Applied Chemistry, vol. 85, No. 6, pp. 914-920, 2012 (Year: 2012).*

Levin et al., "Charge transfer processes on electrodes modified by polymer films of metal complexes with Schiff bases," Electrochmica Acta 109 (2013) 153-161.

Malyushevskaya et al., "Production of metal-carbon composite nanomaterials by the electrodischarge method," Surface Engineering and Applied Electrochemistry, 49(4):278-282, 2013.

Russian Search Report with English translation for Russian Application No. 201708436/05(014689), May 3, 2018, 4 pages.

Russian Office Action with English translation for Russian Application No. 201708436/05(014689), May 3, 2018, 14 pages.

Karushev et al., "Adsorption-Electrochemical Modification of Nanoporous Carbon Materials by Nickel Complexes with Schiff Bases," Russian Journal of Applied Chemistry, 85(6):914-920, 2012.

(Continued)

*Primary Examiner* — Ling X Xu
(74) *Attorney, Agent, or Firm* — Erickson Law Group, PC

(57) ABSTRACT

A method for creating a metal-carbon composite. In one embodiment, the method includes the steps of providing a polymer Schiff base transition metal [film] *complex* precursor *film* having a chemical structure of the formula $[M(Schiff)]_n$ and a recurring unit and a transition metal selected from the group consisting of nickel, palladium, platinum, cobalt, copper, iron; Schiff is a tetradentate Schiff base ligand selected from the group consisting of Salen (residue of bis(salicylaldehyde)-ethylenediamine), Saltmen (residue of bis(salicylaldehyde)-tetramethylethylenediamine, Salphen (residue of bis-(salicylaldehyde)-o-phenylenediamine), a substituent in a Schiff base is selected from the group consisting of H—, and carbon-containing substituents, preferably $CH_3$—, $C_2H_5$—, $CH_3O$—, $C_2H_5O$—, and Y is a bridge in a Schiff base depositing the polymer Schiff base transition metal precursor film onto a support substrate; and heating the polymer Schiff base transition metal *complex* precursor film and support substrate in a furnace in an inert atmosphere.

14 Claims, No Drawings

(56) References Cited

OTHER PUBLICATIONS

Marvel et al., "Quadridentate and Sexadentate Chelates. Some Preliminary Studies in their Preparation and Thermal Stability," Journal of the American Chemical Society, 78(19):4905-4909, 1956.

PCT International Search Report and the Written Opinion of the International Searching Authority for International Application No. PCT/US2015/044997, date of mailing: Nov. 18, 2015, 16 pages.

* cited by examiner

METHOD OF PRODUCING POROUS METAL-CARBON MATERIALS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application *is a reissue application of U.S. Pat. No. 9,653,736, filed Aug. 13, 2015 and issued May 16, 2017, which* claims priority to U.S. Provisional Application 62/039,010, filed Aug. 19, 2014, the entire contents of which are herein incorporated by reference in their entirety.

FIELD OF INVENTION

This invention relates to methods of producing porous metal-carbon materials with high electric conductivity and high specific surface area with controllable pore size distribution.

BACKGROUND OF THE INVENTION

Porous carbon materials (CMs) with high specific surface area are widely used for many electrochemical, catalytic, and adsorption applications. The preparation of such materials usually involves two steps: 1) formation of carbon via carbonization of precursor material; 2) activation of carbon in order to enhance its surface area.

Porous CMs may be produced via carbonization of naturally occurring raw materials, such as wood, petroleum pitch, peat, and other sources of high carbon content. A major advantage of CMs prepared from naturally occurring raw materials is their relatively low cost. At the same time, such CMs contain large amounts of impurities such as sulfur, nitrogen, phosphor and metal salts, which initially reside in the precursor material. Such impurities may introduce undesirable side reactions when carbon material is employed, for example, in energy storage devices such as lithium-ion batteries, fuel cells or double layer capacitors. These side reactions may deteriorate the structure and lower the performance of the device.

Porous CMs may also be formed by carbonizing synthetic materials of high carbon content, for example polymers, at very high temperatures in a non-oxidative (inert) atmosphere, for example nitrogen, argon, or helium. The most widely-employed synthetic polymer precursor for making CMs is polyacrylonitrile. Other precursors such as phenolic resin and polyacetylenes may also be used. The disadvantage of CMs made from synthetic polymers is that these CMs have a very low specific surface area.

To enhance the surface area of CMs, activation is always performed after the carbonization process. The physical activation is accomplished with steam, carbon monoxide (CO), carbon dioxide ($CO_2$), and $CO_2$-containing gases. The chemical activation agents are $ZnCl_2$, $H_2SO_4$, $H_3PO_4$, NaOH, LiOH, KOH, $N_xO_y$, [x=1-2, y=1-3], $Cl_2$ and other halogens. Activation provides for enhanced surface area of CMs, but it can introduce defects or completely destroy a formed carbon body.

To be useful for electrochemical and catalytic applications, the resulting high surface area CM should have the following properties: nano- or molecular-level organization of carbon structure, with structural elements (carbon fragments) ranging in size from 1 nm (molecular dimensions) to 10-100 nm (nano dimensions); regulated distribution of structural elements (carbon fragments), that can be adjusted to suit the material application; narrow pore size distribution; high electronic conductivity; high chemical stability and mechanical strength; and low cost.

A major problem in many carbon material applications is a relatively high internal resistance of CMs, which can be lowered through use of metal-carbon materials (MCMs). Uniform imbedding of metal atoms in the form of, for example, nano-sized particles or clusters into the porous carbon structure also improves and expands the catalytic properties of the discussed MCMs.

Various fabrication techniques for preparation of metal-carbon materials have been disclosed. One of the methods of fabrication implies thermal catalytic decomposition of hydrocarbons in the microporous metal matrix. One method describes the synthesis of MCM by thermal chemical vapor deposition of ethane in the presence of hydrogen at 660° C. on sintered metal fiber filters of nickel and Ni-containing alloys.

Another technique implies impregnation of high surface area porous carbon with metal precursors (metal salts or metal complexes) followed by their reduction to pure metals or metal oxides. For example, one method describes the approach where the carbon fiber material is dipped into an aqueous solution of ruthenium chloride followed by thermal decomposition to ruthenium oxide formed in the pores of the carbon fibers.

The majority of fabricated metal-carbon materials have metal-carbon globules or fibers of different pre-defined dimensions, but the relative distribution of globules (or fibers) is chaotic and difficult to regulate. This difficulty in regulation prevents the preparation of MCMs with pre-defined and controllable properties that suit the material application, which in turn limits the widespread use of these materials.

The present invention addresses this need.

SUMMARY OF THE INVENTION

One aspect of the present invention is a method for producing a porous metal-carbon material (MCM) having high electronic conductivity, a high specific surface area, controllable elementary composition, a uniform distribution of metal atoms inside the MCM, and controllable pore size distribution, based on the requirements of specific applications.

In one embodiment, a method for producing a porous metal-carbon material includes carbonizing a polymer grown on a support; the polymer being a polymer Schiff base transition metal complex. In one embodiment, carbonizing is accomplished by heating the support-mounted polymer under a non-oxidative (inert) atmosphere at a temperature ranging from 500° C. to 750° C. for a time period sufficient to form a metal-carbon material on the support.

In various embodiments, metal-carbon composite materials of this invention are made from polymer Schiff base transition metal complexes (hereinafter referred to as poly [M(Schiff)], where M is a transition metal and Schiff is a tetradentate Schiff base ligand) grown by oxidative electrochemical polymerization of corresponding square-planar monomer complexes on the surface of an inert electrically conducting support.

In other embodiments, poly[M(Schiff)] polymers have high carbon content, metal atoms evenly distributed throughout the polymer structure, high surface area, and uniform distribution of structural elements along the surface of the support. Structural elements of poly[M(Schiff)] polymers are individual stacks arranged perpendicular to the support surface. Each stack is formed from monomer square-planar fragments [M(Schiff)] via donor-acceptor interactions between a metal center of one monomer fragment and a phenyl ring of a ligand that is part of another monomer fragment. The length and diameter of the stacks and the distance between the stacks are pre-defined by the monomer composition and polymerization conditions (polymerization potential, polymerization regime, supporting electrolyte, and solvent).

Polymer Schiff base transition metal complexes are thermally stable at temperatures below 370° C. When these polymers are heated at higher temperatures in a non-oxidative (inert) atmosphere, the carbonization of the polymers begins. The carbonization includes the decomposition the organic portion of the polymer accompanied by evolving hydrogen, oxygen and nitrogen. The result of a complete carbonization of a poly[M(Schiff)] polymer is the formation of a metal-carbon material.

The geometry of the resulting metal-carbon material closely resembles the geometry of the initial polymer. In the process of carbonization, polymer stacks turn into pillar-like elements consisting of carbon and metal atoms, and a MCM composed of structural elements having steric and geometrical resemblance to the polymer stacks is formed. The diameter of said elements is from 1 to 1.5 nanometers and is determined by the diameter of stacks in the precursor polymer. The length of said elements is up to 50 micrometers and determined by the thickness of the precursor polymer film. The elements are spaced at a distance from 0.2 to 10 nanometers from each other, which corresponds to the initial distribution of polymer stacks along the surface of the support. The regular spacing between pillar-like elements makes the produced metal-carbon material highly porous, with uniform pore size distribution in the nanopore region. The preservation of the initial polymer geometry in the resulting MCM is provided by the carbonization of the support-mounted poly[M(Schiff)] polymer, the support being the support used for growing the polymer.

The result of the present invention is the formation of the metal-carbon material on the support, with said metal-carbon material having the following properties: specific electrochemically-active surface area between 50 $m^2/g$ and 2,500 $m^2/g$; a carbon content from 50 to 85 weight percent; a metal-to-carbon weight ratio from 0.2 to 1.0; a controllable regular structure comprised of pillar-like elements having a diameter of 1 to 1.5 nanometers, length up to 50 micrometers, placed at a distance from 0.2 to 10 nanometers from each other along the support surface; and a uniform distribution of metal clusters with a chemical formula $MC_n$, wherein M is a metal atom, C is a carbon atom, and (n) is a number from 0.5 to 6 inside the metal-carbon material.

The presence of metal atoms evenly distributed throughout the metal-carbon material results in high electronic conductivity of the MCM.

These and other objects and features of the present invention will be more apparent from a detailed description that follows.

DETAILED DESCRIPTION OF THE INVENTION

Polymer Schiff base transition metal complexes, precursors used to make metal-carbon materials of this invention, have a chemical structure characterized by the formula $[M(Schiff)]_n$ and the recurring unit of the following structure:

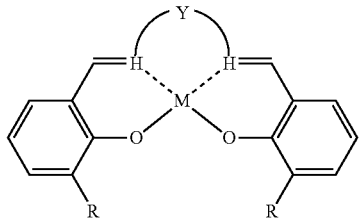

wherein n is an integer between 2 and 50,000; M is a transition metal selected from the group consisting of nickel, palladium, platinum, cobalt, copper, iron; Schiff is a tetradentate Schiff base ligand selected from the group consisting of Salen (residue of bis(salicylaldehyde)-ethylenediamine), Saltmen (residue of bis(salicylaldehyde)-tetramethylethylenediamine, Salphen (residue of bis-(salicylaldehyde)-o-phenylenediamine), R is a substituent in a Schiff base selected from the group consisting of H—, and carbon-containing substituents, preferably $CH_3$—, $C_2H_5$—, $CH_3O$—, $C_2H_5O$—, and Y is a bridge in a Schiff base and has the following structure:

—$CH_2$—$CH_2$— in Salen

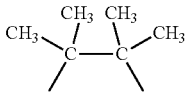

in Saltmen

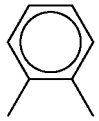

in Salphen

Structural elements of the polymer Schiff base transition metal complexes (poly[M(Schiff)]) are individual stacks arranged perpendicular to the support surface. Each stack is formed from monomer square-planar fragments [M(Schiff)] via donor-acceptor interactions between a metal center of one monomer fragment and a phenyl ring of a ligand that is part of another monomer fragment. Charge transfer in polymer Schiff base transition metal complexes occurs via "electron hopping" between metal centers with different oxidation states (redox conductivity). Oxidation or reduction of polymer metal complexes associated with the change in the oxidation states of metal centers is accompanied by ingress/egress of charge-compensating counter-ions of electrolyte solution into/out of the polymer film to maintain overall electrical neutrality of the system.

Poly[M(Schiff)] polymers structured at the molecular level, i.e. with uniform controllable distribution of structural elements (stacks) on the support surface, can be grown by using different strategies of the oxidative electrochemical polymerization of Schiff base transition metal complexes. These polymers have high carbon content, high surface area, and metal atoms evenly distributed throughout the polymer structure.

The method of preparing the metal-carbon material of the present invention comprises the carbonization of a polymer grown on a support, with said polymer being a polymer Schiff base transition metal complex, accomplished by heating the support-mounted polymer under a non-oxidative (inert) atmosphere at an elevated temperature.

The precursor polymer for producing the metal-carbon material is preferably in the form of a polymer film grown on a support by oxidative electrochemical polymerization. The polymer film thickness is limited by the distance, at which the initial controllable distribution of structural elements (stacks) is preserved (usually, up to 50 micrometers).

The support is selected from the group consisting of electronically conductive materials, such as carbon, including glassy carbon, carbon fibers, carbon fibrils, and other carbon materials, carbon materials with metal coatings, and metals, more preferably metals electrochemically inert at the potentials of the polymerization.

The precursor polymer for producing the metal-carbon material is preferably in the form of a polymer structured at the molecular level, with required elemental composition and pre-defined distribution of structural elements (stacks) on the support surface, based on the requirements of the MCM application.

The support-mounted precursor polymer is then transferred to a container, preferably a tube furnace, that is filled with a non-oxidizing atmosphere including nitrogen, argon, or helium, and heated to elevated temperatures ranging from 500° C. to 750° C., preferably from 550° C. to 650° C., and more preferably from 580° C. to 620° C. Upon reaching the required temperature, the heating is conducted at this temperature for the time period sufficient to fully accomplish the carbonization of the precursor polymer; typically, between 1 and 4 hours, and preferably between 2 and 3 hours.

"Carbonization" is defined herein as increasing the carbon content in the precursor material by heating it in a non-oxidizing environment to elevated temperatures, during which hydrogen, oxygen and nitrogen are evolved. The reaction product after fully accomplished carbonization of a polymer Schiff base transition metal complex is a metal-carbon material.

The geometry of the resulting metal-carbon material closely resembles the geometry of the initial polymer. In the process of carbonization, polymer stacks turn into pillar-like elements consisting of carbon and metal atoms, and a MCM composed of structural elements having steric and geometrical resemblance to the polymer stacks is formed. The diameter of the elements is from 1 to 1.5 nanometers and is determined by the diameter of stacks in the precursor polymer. The length of the elements is up to 50 micrometers and is determined by the thickness of the precursor polymer film. The elements are spaced at a distance from 0.2 to 10 nanometers from each other, which corresponds to the initial distribution of polymer stacks along the surface of the support. The regular spacing between pillar-like elements makes the resulting metal-carbon material highly porous, with uniform pore size distribution in the nanopore region. The preservation of the initial polymer geometry in the resulting MCM is provided by performing carbonization of the support-mounted poly[M(Schiff)] polymer, the support being the support used for growing the polymer.

The resulting metal-carbon material has a high carbon content from 50 to 85 weight percent and a metal-to-carbon weight ratio from 0.2 to 1.0, as determined by the chemical composition of the precursor polymer. The metal atoms are uniformly distributed inside the composite material and exist in the form of metal clusters with a chemical formula $MC_n$, wherein M is a metal atom, C is a carbon atom, and (n) is a number from 0.5 to 6. The presence of dispersed metal atoms in the structure of the MCM results in higher electronic conductivity of the metal-carbon material than that of conventional porous CMs.

The resulting metal-carbon composite material can have a specific electrochemically-active surface area between 50 $m^2/g$ and 2,500 $m^2/g$, without any additional activation. "Electrochemically-active surface area" is defined herein as an internal surface area accessible for ions of the supporting electrolyte in an electrochemical experiment. The value of a specific electrochemically-active surface area is calculated using the value of specific double-layer capacity determined by cyclic voltammetry investigation of the MCM sample in the acetonitrile solution containing 0.1 mol/L of tetraethylammonium tetrafluoroborate.

The parameters of the process of producing the metal-carbon material of this invention significantly affect the properties of the final product.

The carbonization temperature affects the carbon content and the value of specific electrochemically-active surface area in the MCM. The process performed at temperatures that are lower than required for the effective carbonization of a given polymer results in the formation of an under-carbonized MCM. Such under-carbonized material retains a portion of hydrogen, oxygen, and nitrogen atoms, which lowers the ultimate carbon yield. The under-carbonized material also retains a portion of the insulating polymer that has already lost redox conductivity but has not yet acquired electronic conductivity. As a result, the final MCM has relatively low electronic conductivity and decreased value of specific electrochemically-active surface area. Heating the precursor polymer to temperatures that are higher than required for the effective carbonization of a given polymer results in agglomeration of individual structural elements, which results in low porosity of the final metal-carbon material.

The carbonization process performed at a required temperature for an insufficient time period also leads to the formation of under-carbonized MCM with lower carbon content and decreased specific electrochemically-active surface area.

The porosity of the final metal-carbon material also depends on the precursor polymer properties. As discussed above, the properties of poly[M(Schiff)] polymers can be effectively controlled by altering the conditions of the polymerization, such as monomer structure, polymerization regime, supporting electrolyte, and solvent.

The metal-carbon materials of the present invention can be utilized as base or main materials for catalytic and other applications that demand a high surface area with a controlled porosity.

Other areas of the application of metal-carbon materials are energy production and energy storage, such as electrodes for fuel cells, double layer capacitors, lithium-ion, and lithium-polymer batteries.

Ultimately, the properties of the metal-carbon materials of the present invention can be effectively controlled based on the requirements of specific applications.

The selectivity of metal-carbon materials of the present invention in catalytic applications can be provided by altering a metal center in the precursor polymer. For example, nickel-containing MCMs will be most effective as catalysts for hydrogenation processes, whereas palladium-containing MCMs will effectively catalyze the oxidation of methanol. The accessibility of metal catalytic centers for substrate molecules and high rates of diffusion of substrates and reaction products inside the solid-state catalyst can be ensured by using metal-carbon materials with large pores and relatively low specific electrochemically-active surface area.

The metal-carbon materials with high specific electrochemically-active surface area are most effective for applications in energy-producing and energy-storage devices that normally require high porosity and high specific surface area of electrode material.

The following examples illustrate the present invention, but should not be construed as limiting the invention:

EXAMPLES

Example 1

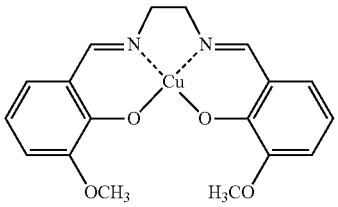

A polymer film with a formula poly[Cu($CH_3$O-Salen)] and a recurring unit was employed to prepare a metal-carbon material. The polymer film having the thickness of 0.8 micrometers and mass of $2\times10^{-5}$ g was initially deposited onto a glassy carbon plate having the dimensions of 1 centimeter by 0.5 centimeter by 0.04 centimeter so that the polymer occupied the area of 0.5 centimeter by 0.5 centimeter on one side of the plate. The polymerization was accomplished by applying the constant potential of +0.98 V (vs. a standard silver/silver chloride reference electrode) to the glassy carbon plate in the acetonitrile solution containing 0.1 mol/L of tetraethylammonium tetrafluoroborate and 0.001 mol/L of the monomer complex [Cu($CH_3$O-Salen)]. The support with a polymer film on it was carefully rinsed with acetonitrile to remove any traces of the monomer and supporting electrolyte and placed in the tube furnace filled with high-purity nitrogen. The polymer was carbonized at 600° C. for 3 hours. The final metal-carbon material contained 77 wt % of carbon and had a specific electrochemically-active surface area of 2000 $m^2$/g.

Example 2

The polymer synthesized following the same procedures as those in Example 1 was employed to prepare a metal-carbon material. The polymer was carbonized at 500° C. for 3 hours. The final metal-carbon material contained 64 wt % of carbon and had a specific electrochemically-active surface area of 1000 $m^2$/g. The carbonization at a lower temperature than that employed in Example 1 results in incomplete carbonization. As a result, the polymer lost redox conductivity before the carbon matrix was fully formed, resulting in low electronic conductivity of the final metal-carbon material.

Example 3

The polymer synthesized following the same procedure as that in Example 1 was employed to prepare a metal-carbon material. The polymer was carbonized at 700° C. for 3 hours. The final metal-carbon material contained 77 wt % of carbon and had a specific electrochemically-active surface area of 500 $m^2$/g. The carbonization at a higher temperature than that employed in Example 1 lead to agglomeration of individual structural elements, which resulted in low porosity of metal-carbon material.

Example 4

The same procedures as that in Example 1 were followed with the exception that the precursor polymer film had the thickness of 0.4 micrometers and mass of $1\times10^{-5}$ g. The polymer was carbonized at 600° C. for 3 hours. After carbonization, the metal-carbon material contained 77 wt % of carbon and had a specific electrochemically-active surface area of 2000 $m^2$/g. The comparison of these results with the results of Example 1 demonstrates that the porosity of the metal-carbon material does not depend on the thickness of the precursor polymer film, but is rather defined by the initial distribution of structural elements (stacks) in the polymer.

Example 5

The same procedures as those in Example 1 were followed with the exception that the polymerization solution contained propylene carbonate instead of acetonitrile, and the mass of the formed 0.8 micrometer precursor polymer film was $7.5\times10^{-6}$ g. After carbonization, the metal-carbon material contained 77 wt % of carbon and had a specific electrochemically-active surface area of 750 $m^2$/g. The larger solvent molecules (propylene carbonate) in the polymerization solution compared to the solvent employed in Example 1 (acetonitrile) provide greater distances between the structural elements (stacks) of the precursor polymer. This results in the increased pore size in the final metal-carbon material but a decreased amount of electroactive material per square centimeter of the support, which is reflected in the low value of a specific electrochemically-active surface area of the composite.

Example 6

A polymer film had a formula poly[Cu($CH_3$O-Saltmen)] and a recurring unit was

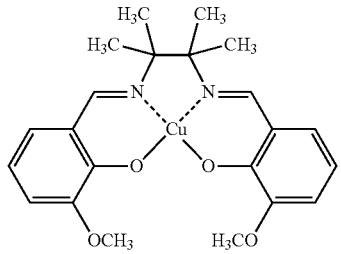

employed to prepare a metal-carbon material. The polymer film having the thickness of 0.8 micrometers and mass of $2.2\times10^{-5}$ g was preliminary deposited onto a glassy carbon plate having the dimensions 1 centimeter by 0.5 centimeter by 0.04 centimeter so that the polymer occupied the area of 0.5 centimeter by 0.5 centimeter on one side of the plate. The polymerization was accomplished by applying the constant potential of +1.00 V (vs. a standard silver/silver chloride reference electrode) to the glassy carbon plate in the acetonitrile solution containing 0.1 mol/L of tetraethylammonium tetrafluoroborate and 0.001 mol/L of the monomer complex [Cu($CH_3O$-Saltmen)]. The support with a polymer film on it was carefully rinsed with acetonitrile to remove any traces of the monomer and supporting electrolyte and placed in the tube furnace filled with high-purity nitrogen. The polymer was carbonized at 600° C. for 3 hours. The final metal-carbon material contained 81 wt % of carbon and had a specific electrochemically-active surface area of 1200 $m^2/g$. The repulsive interactions between monomer fragments caused by the presence of four additional methyl groups in the ligand portion of the monomer provide greater distances between the structural elements (stacks) in the precursor polymer with a formula poly[Cu($CH_3O$-Saltmen)] as compared with the precursor polymer with a formula poly[Cu($CH_3O$-Salen)] employed for the synthesis of a metal-carbon material in Example 1. This results in the increased pore size in the final metal-carbon material but a decreased amount of electroactive material per square centimeter of the support, which is reflected in the low value of a specific electrochemically-active surface area of the composite.

Example 7

A polymer film with a formula poly[Ni(Salen)] and a recurring unit of

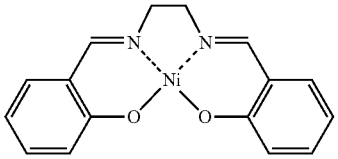

was employed to prepare a metal-carbon material. The polymer film having the thickness of 0.8 micrometers and mass of $1.7\times10^{-5}$ g was initially deposited onto the glassy carbon plate having the dimensions 1 centimeter by 0.5 centimeter by 0.04 centimeter so that the polymer occupied the area of 0.5 centimeter by 0.5 centimeter on one side of the plate. The polymerization was accomplished by applying the constant potential of +1.00 V (vs. a standard silver/silver chloride reference electrode) to the glassy carbon plate in the acetonitrile solution containing 0.1 mol/L of tetraethylammonium tetrafluoroborate and 0.001 mol/L of the monomer complex [Ni(Salen)]. The support with a polymer film on it was carefully rinsed with acetonitrile to remove any traces of the monomer and supporting electrolyte and placed in the tube furnace filled with high-purity nitrogen. The polymer was carbonized at 600° C. for 3 hours. The final metal-carbon material contained 77 wt % of carbon and had a specific electrochemically-active surface area of 2500 $m^2/g$.

Example 8

The same procedures as those in Example 7 were followed with the exception that the polymerization solution contained 0.1 mol/L of tetraethylammonium hexafluorophosphate instead of 0.1 mol/L of tetraethylammonium tetrafluoroborate, and the mass of the formed 0.8 micrometer precursor polymer film was $1.2\times10^{-5}$ g. After carbonization, the metal-carbon material contained 77 wt % of carbon and had a specific electrochemically-active surface area of 1700 $m^2/g$. The larger anions of supporting electrolyte (hexafluorophosphate ions) in the polymerization solution compared to the anions of the electrolyte employed in Example 7 (tetrafluoroborate ions) provide greater distances between the structural elements (stacks) of precursor polymer. This results in the increased pore size in the final metal-carbon material but a decreased amount of electroactive material per square centimeter of the support, which is reflected in the low value of a specific electrochemically-active surface area of the composite.

Unless otherwise indicated, all numbers expressing lengths, widths, depths, or other dimensions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The terms "a," "an," "the," and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known to the inventor for carrying out the spirit of the present disclosure. Of course, variations on these described embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method for creating a metal-carbon composite comprising the steps of:

a. providing a polymer Schiff base transition metal [film] *complex* precursor *film* having a chemical structure of the formula $[M(Schiff)]_n$ and the recurring unit of the following structure:

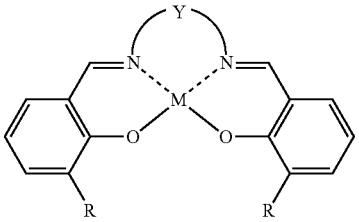

wherein n is an integer between 2 and 50,000; M is a transition metal selected from the group consisting of nickel, palladium, platinum, cobalt, copper, and iron; Schiff is a tetradentate Schiff base ligand selected from the group consisting of Salen (residue of bis(salicylaldehyde)-ethylenediamine), Saltmen (residue of bis(salicylaldehyde)-tetramethylethylenediamine, and Salphen (residue of bis-(salicylaldehyde)-o-phenylenediamine); R is a substituent in a Schiff base selected from the group consisting of H—[;], and carbon-containing substituents, preferably $CH_3$—, $C_2H_5$—, $CH_3O$—, $C_2H_5O$—; and Y is a bridge in a Schiff base and has the following structure:

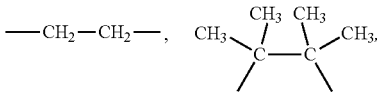

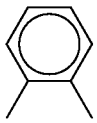

or when the Schiff base is a Salen, a Saltmen and a Salphen, respectively, b. depositing the polymer Schiff base transition metal *complex* precursor film onto a support substrate; and c. heating the polymer Schiff base transition metal *complex* precursor film and support substrate in a furnace in an inert atmosphere.

2. The method of claim 1 wherein the support substrate is a glassy carbon plate.

3. The method of claim 1 wherein the inert atmosphere is selected from one or more of nitrogen, argon, and helium.

4. The method of claim 1 wherein the polymer Schiff base transition metal *complex* precursor film and support substrate are heated between 500° C.-750° C. for 1-4 hours.

5. The method of claim 4 wherein the polymer Schiff base transition metal *complex* precursor film and support substrate are heated from 550° C. to 650° C.

6. The method of claim 4 wherein the polymer Schiff base transition metal *complex* precursor film and support substrate are heated from 580° C. to 620° C.

7. The method of claim 4 wherein the polymer Schiff base transition metal *complex* precursor film and support substrate are heated for 2-3 hours.

8. The method of claim 1 wherein the deposition of the polymer Schiff base transition metal *complex* precursor film onto a support substrate comprises polymerization by application of a constant potential to the substrate.

9. The method of claim 8 wherein the support substrate is a glassy carbon plate.

10. The method of claim 8 wherein the constant potential of +0.98V, as measured against a standard silver/silver chloride reference electrode, is applied to the substrate.

11. The method of claim 8 wherein the polymerization of a polymer *complex* film occurs with the substrate positioned in a solution containing tetraethylammonium tetrafluoroborate and the Schiff base monomer complex.

12. The method of claim 11 where a solvent of the solution is acetonitrile.

13. The method of claim 12 wherein the support with the polymer *complex* film on it is rinsed with acetonitrile prior to being placed in the furnace.

14. The method of claim 11 where a solvent of the solution is propylene carbonate.

* * * * *